United States Patent
Gruning et al.

(10) Patent No.: US 6,242,499 B1
(45) Date of Patent: Jun. 5, 2001

(54) POLYGLYCEROL PARTIAL ESTERS OF FATTY ACIDS AND POLYFUNCTIONAL CARBOXYLIC ACIDS, THEIR PREPARATION AND USE

(75) Inventors: Burghard Gruning; Peter Hameyer; Josef Metzelaars; Christian Weitemeyer, all of Essen (DE)

(73) Assignee: Goldschmidt AG, Essen (DE)

( * ) Notice: Subject to any disclaimer, the term of this patent is extended or adjusted under 35 U.S.C. 154(b) by 0 days.

(21) Appl. No.: 08/936,270

(22) Filed: Sep. 24, 1997

(30) Foreign Application Priority Data

Oct. 9, 1996 (DE) .............................................. 196 41 604

(51) Int. Cl.[7] .......................... A61K 47/00; A61K 6/00; B01F 17/00; C07C 67/00

(52) U.S. Cl. ....................... 514/785; 514/937; 424/401; 516/22; 516/21; 516/31; 516/33; 554/115; 554/124; 554/227

(58) Field of Search ............................... 514/772.2, 938, 514/785, 937; 424/59, 401; 516/21, 22, 31, 33; 554/115, 124, 227

(56) References Cited

U.S. PATENT DOCUMENTS

| 3,890,358 | * | 6/1975 | Hutchinson .............................. 424/64 |
| 4,643,850 | * | 2/1987 | Hulsmann et al. ................ 260/410.7 |
| 4,931,210 | | 6/1990 | Takahashi et al. .................... 252/314 |
| 4,971,721 | | 11/1990 | Takahashi et al. .................... 252/314 |
| 4,985,173 | | 1/1991 | Takahashi et al. .................... 252/314 |
| 4,988,456 | | 1/1991 | Takahashi et al. .................... 252/314 |
| 5,155,246 | | 10/1992 | Naskar et al. ......................... 554/213 |
| 5,391,321 | | 2/1995 | Gruning et al. ....................... 252/309 |

FOREIGN PATENT DOCUMENTS

| 40 12 693 | 10/1991 | (DE) ................................. C07C/0/67 |
| 40 29 323 | 3/1992 | (DE) . |
| 41 17 033 | 11/1992 | (DE) . |
| 44 09 569 | 8/1995 | (DE) . |
| 0 440 203 | 8/1991 | (EP) . |
| WO 95/34528 | 12/1995 | (WO) ................................ A61K/7/00 |

OTHER PUBLICATIONS

JP 03074315, Nishida, Minoru et al, Skin moisturizing cosmetic and transdermal preparations containing (poly) glycerin esters.AN 1991: 663077 HCAPLUS, see enclosed abstract and bibliography data, Mar. 1991.*

\* cited by examiner

*Primary Examiner*—Russell Travers
*Assistant Examiner*—Shengjun Wang
(74) *Attorney, Agent, or Firm*—Scully, Scott, Murphy & Presser

(57) ABSTRACT

The invention relates to polyglycerol partial esters of saturated or unsaturated, linear or branched fatty acids and polyfunctional carboxylic acids, which are obtainable by esterification of a polyglycerol mixture with saturated or unsaturated, linear or branched fatty acids having 12 to 22 carbon atoms and polyfunctional carboxylic acids having 4 to 54 carbon atoms and a mean functionality of from 2 to 2.4, the degree of esterification of the polyglycerol mixture being between 30 and 75%.

10 Claims, No Drawings

POLYGLYCEROL PARTIAL ESTERS OF FATTY ACIDS AND POLYFUNCTIONAL CARBOXYLIC ACIDS, THEIR PREPARATION AND USE

FIELD OF THE INVENTION

The invention relates to polyglycerol partial esters of fatty acids and polyfunctional carboxylic acids, obtainable by est-erification of a polyglycerol mixture with saturated or unsaturated, linear or branched fatty acids having 12 to 22 carbon atoms and aliphatic polyfunctional carboxylic acids having 4 to 54 carbon atoms, the degree of esterification of the polyglycerol mixture being between 30 and 75%, to their preparation and use as W/O emulsifiers in cosmetic or pharmaceutical preparations and as auxiliaries for dispersing inorganic micropigments in oil dispersions.

BACKGROUND OF THE INVENTION

For ecological reasons, there is considerable interest, both from the producers and the consumers of emulsion preparations, in W/O emulsifiers which are based on natural raw materials. For this reason, despite their mediocre efficacy, partial esters of polyalcohols, such as glycerol, polyglycerol, sorbitol or methylglycoside, and fatty acids, such as oleic or isostearic acid, are still finding diverse uses.

This type of emulsifier is not suitable, for example, for flowable emulsions (lotions) or for creams with a high content of natural triglycerides. The creams which satisfy the stability requirements of the market (temperature stability of from −15 to +45° C., sometimes from −25 to +50° C.) contain as the oleophilic components largely paraffin oils and fatty acid esters of monoalkanols (MW<500); these have more favorable technological properties than the higher-molecular-weight triglycerides. Nevertheless, for stabilization purposes, relatively high concentrations of viscosity-increasing waxes ($\geq 3\%$) are required, which have an adverse effect on the application properties, since they produce an undesired sticky, greasy feel on the skin.

Coemulsifiers, in particular ethylene oxide adducts in combination with metal soaps, merely broaden the range of applications to paraffin oil-containing lotions.

The emulsifying properties of the polyalcohol-fatty acid partial esters are considerably exceeded by the polyglycerol esters of dimerized and polymerized unsaturated $C_{18}$-fatty acids. They are obtained from the mono-and diglycerides of vegetable oils, preferably soya oil, by thermal treatment at approximately 300° C. over several hours or by transesterification of a thermally polymerized vegetable oil with polyglycerol.

The polyglycerol polyricinoleates formed from castor oil by an analogous process are also effective W/O emulsifiers (DE-B-44 09 659). Because of their sensitivity to oxidation and their pronounced greasy, rancid odour, neither class of substances has been able to establish itself for use in cosmetic or pharmaceutical emulsion preparations. The main factors responsible for this are massive thermal stress during preparation and the unsaturated nature (iodine number approximately 100).

Polyglycerol polyhydroxystearate (Henkel), which is chemically related to polyglycerol polyricinoleate and can likewise be prepared from vegetable raw materials, has, by contrast, a satisfactory sensory quality and in principle is capable of forming cream-like and in particular flowable W/O emulsions.

BRIEF SUMMARY OF THE INVENTION

It was an object of the invention to provide novel polyglycerol partial esters which can be prepared from natural raw materials and, compared with polyglycerol polyhydroxystearate exhibit the additional advantage of improved stability, in particular higher freeze-thaw stability, of the W/O emulsions prepared therewith. This improvement is of considerable practical interest for the transportability and shelf life of the emulsion preparations.

Extended storage at very low temperatures or extreme temperature changes during relatively long transport distances can cause the inadequate emulsion stability to become apparent, namely through significant water separation in the emulsion preparation, or can even result in complete emulsion break-down, which is avoided by the novel solution to the-object.

The invention relates to polyglycerol partial esters with both saturated or unsaturated, linear or branched fatty acids and polyfunctional carboxylic acids, obtainable by esterification of a polyglycerol mixture with saturated or unsaturated, linear or branched fatty acids having 12 to 22 carbon atoms and polyfunctional carboxylic acids having 4 to 54 carbon atoms and a mean functionality of from 2 to 2.4, the degree of esterification of the polyglycerol being between 30 and 75%.

DETAILED DESCRIPTION OF THE INVENTION

Particularly suitable saturated fatty acid components are lauric acid, tridecanoic acid, myristic acid, palmitic acid, margaric acid, stearic acid, arachidic acid and behenic acid and mixtures thereof. Naturally occurring mixtures are, for example, the coconut fatty acids, which contain lauric acid as the main constituent and also contain saturated $C_{14}$- to $C_{18}$-fatty acids and possibly small amounts of saturated $C_8$- to $C_{18}$-fatty acids and unsaturated fatty acids, and tallow fatty acids, which are essentially a mixture of palmitic acid and stearic acid. Particular preference is given to a mixture which comprises at least 40% by weight, preferably from 60 to 99% by weight, of stearic acid.

Suitable unsaturated fatty acid components are monoolefinically unsaturated acids, for example hexadecenoic acids, octadecenoic acids, such as oleic acid (cis-9-octadecenoic acid) or eladidic acid (trans-9-octadecenoic acid), eicosenoic acids and docosenoic acids, such as erucic acid (cis-13-docosenoic acid) or brassidic acid (trans-13-docosenoic acid), poly-unsaturated fatty acids, for example octadecadienoic acids and octadecatrienoic acids, such as linoleic acid and linolenic acid, and mixtures thereof. The best results are obtained with a fatty acid or fatty acid mixture which comprises at least 60% by weight, preferably from 65 to 99% by weight, of oleic acid or erucic acid.

The liquid fatty acids which contain 18 to 22 carbon atoms, namely oleic, ricinoleic, erucic and isostearic acids, are particularly suitable. Because of branching solidification points are below 35° C. It is also possible to use fatty acid mixtures, which can also contain wax-like components, such as hydrogenated ricinoleic acid.

The aliphatic dicarboxylic acids used for the esterification should have at least 4 carbon atoms. They can be straight-chain or branched, such as, for example, malonic acid, succinic acid, fumaric acid, dimethylglutaric acid or trimethyladipic acid, and their anhydrides.

The dicarboxylic acids used can also be dimer fatty acids. As is known, these are mixtures of acyclic and cyclic dicarboxylic acids which are obtained by a catalyzed dimerization reaction of unsaturated fatty acids having 12 to 22 carbon atoms.

For the preparation and use of dimer acids and their physical and chemical properties, reference is made to the publication "The Dimer Acids: The chemical and physical properties, reactions and applications", Ed. E. C. Leonard; Humko Sheffield Chemical, 1975, Memphis, Tenn.

The dicarboxylic acids can also contain, to a lesser extent, tri-and polyfunctional carboxylic acids. The functionality of the mixture should not exceed a value of 2.4 molar average.

A particularly suitable emulsifier for the intended use according to the invention is dimer acid or a mixture of dimer and trimer acids (e.g. Pripol products from Unichema), which is obtained from vegetable oils with a high content of unsaturated $C_{18}$-fatty acids (oleic, linoleic and linolenic acid). The significantly higher molecular weights which can be achieved using these acids for a roughly constant number of free hydroxyl groups in the product results in significantly improved stabilization of the phase interfaces in W/O emulsions.

Suitable polyglycerols are in particular those having a mean degree of condensation of $\geq 2$, preferably from 3 to 4. These are technical-grade polyglycerol mixtures which are obtained, for example, by alkali-catalyzed condensation of glycerol at elevated temperatures and from which fractions with the desired degree of condensation can be obtained if desired by distillation methods. Also suitable are polyglycerols obtained by other methods, e.g. from epichlorohydrin or glycidol.

Particularly suitable polyglycerols have the following oligomer distribution:
Glycerol 0 to 30% by weight
Diglycerol 15 to 40% by weight
Triglycerol 10 to 55% by weight
Tetraglycerol 2 to 25% by weight
Pentaglycerol and higher components 0 to 15% by weight In the polyglycerol partial esters according to the invention, from 30 to 75%, preferably from 50 to 65%, of the hydroxyl groups of the polyglycerol are esterified. They are initially esterified to a degree of esterification of from 25 to 60%, preferably from 35 to 50%, using fatty acid and in a second step, using dicarboxylic acids to an overall degree of esterification of from 30 to 75%, preferably from 50 to 65%. Through suitable selection of the hydrophilic and lipophilic molecular proportions, an HLB value of from 3 to 7 is aimed at in order to obtain favorable properties for the stabilization of W/O emulsions.

The polyglycerol partial esters according to the invention can be prepared in a manner known per se by heating the reaction components and removing the resultant water of reaction by distillation. The reaction can be accelerated by means of acidic or basic catalysts, such as sulfonic acids, phosphoric acid or phosphorous acid, Lewis acids, such as tin salts, alkali metal or alkaline earth metal oxides or hydroxides, alcoholates or salts. However, the addition of a catalyst is not absolutely necessary. The polyglycerol partial esters are preferably prepared in a two-step process, which again is carried out in a manner known per se. In a first step, the polyglycerol is esterified using the monofunctional fatty acid or some of the fatty acid. After most, or all, of the fatty acid has reacted, the polyfunctional carboxylic acid is then added and the esterification reaction is continued. The progress of the reaction can be monitored, for example, via the water of reaction removed, by measuring the acid number or by infrared spectroscopy. In general, an acid number in the end product of <20, preferably <10, is desired. Products with an acid number of <5 are particularly preferred.

The polyglycerol esters according to the invention are suitable for stabilizing emulsions and dispersions. They are preferably used as emulsifiers in the preparation of cosmetic or pharmaceutical preparations.

Suitable cosmetic preparations which have a readily spreadable consistency as a result of using oil-in-water or water-in-oil emulsifiers, because these emulsifier systems permit the ready incorporation of an oil or fat into an aqueous phase or an aqueous phase into an oil or a fat, are, for example, creams, such as skin care creams, baby creams or sun-protection creams, ointments, lotions or cosmetics. In pharmaceutical preparations, such as ointments or creams, oil-in-water or water-in-oil emulsifiers are needed to apply active ingredients.

Oil components which can be used include ester oils, such as octyl palmitate, octyl stearate, cetyl octanoate, caprylic/capric acid triglycerides, decyl oleate, cetearyl octanoate, isopropyl myristate, isopropyl palmitate, $C_{12\text{-}13}$-alkyl benzoate, stearyl heptanoate and dibutyl adipate vegetable oils, such as wheatgerm oil, joba oil, olive oil, starflower oil, avocado oil, groundnut oil, almond oil, sunflower oil and walnut oil higher alcohols, such as octyldodecanol (or Guerbet alcohols in general) and oleyl alcohol, and paraffin-like (hydrocarbon) oils, such as paraffin oil, isohexadecanes, polydecenes, vaseline, Paraffinum perliquidum and squalane.

The usual compositions and constituents and the usual auxiliaries and additives, such as stabilizers or preservatives, for cosmetic and pharmaceutical preparations of this type are known to the person skilled in the art and thus need no further explanation here.

At low temperatures, the polyglycerol partial esters used according to the invention exhibit a significantly increased shelf life of the cosmetic and pharmaceutical preparations prepared therewith compared with the prior art, which is of particular importance for water-in-oil emulsions, which are more difficult to stabilize than oil-in-water emulsions. Furthermore, lower concentrations of the polyglycerol partial esters and/or lower quantities of consistency-imparting waxes are generally needed in the preparations in order to achieve the same effect as with agents of the prior art.

The polyglycerol esters according to the invention are also suitable for stabilizing dispersions of a variety of pigments in oils. Preferred pigments are inorganic pigments. Titanium dioxide is particularly preferred. The oil components used can be those listed above.

EXAMPLES

1. Preparation

The polyglycerol ester can be prepared in two stages which proceed in a manner known per se. Firstly, polyglycerol was esterified using fatty acid. 264 g (0.93 mol) of isostearic acid was mixed with 100 g of technical-grade polyglycerol, distinguished by a hydroxyl number of 1180, and heated to 250° C. while nitrogen was passed through the mixture. After reaction for three hours at this temperature, the acid number was 6.4. The reaction mixture was then cooled to 180° C., and 121 g of dimer acid (Pripol 1025 from Unichema, comprising approximately 5% of monocarboxylic acid, approximately 75% of difunctional and approximately 20% of trifunctional carboxylic acid) was added to the reaction mixture. The batch was then heated to 250° C. again and maintained at this temperature for three hours.

An amber-colored, viscous product was obtained which was characterized by a hydroxyl number of 68 and an acid number of 1.5.

2. Technical testing 2.1. W/O emulsifiers

The example formulations below show the variety of applications of the emulsifier according to the invention for preparing skin-care and -protection emulsion preparations.

They comprise:
emulsions with a flowable and pasty consistency (lotions or creams),
emulsions whose oil phase comprises hydrocarbons (paraffin oils), fatty acid monoalkyl esters or fatty acid triglycerides,
preparations whose oil or water phase contains dermatological active ingredients.

These emulsions have extremely high stability to heat and cold. They are stable for at least 5 months at 45° C. and for at least 1 month at 50° C.; they can withstand at least 5 freeze-thaw cycles.

For comparison purposes, the emulsifier polyglyceryl polyhydroxystearate was employed in experiment (I), Fm 6, and the other components were used in the same quantities as in experiment Fm 5 for preparing a flowable emulsion. Comparative experiment Fm 6 showed severe water separation after 1–3 freeze-thaw cycles.

Also for comparison purposes, an emulsifier prepared by esterification of polyglycerol having a degree of condensation of 3 and approximately 3 mol of oleic acid was used in the same quantities as in experiment Fm 3 for preparing a cream. Experiment Fm 7 prepared using this comparative emulsifier displayed water separation after 3 months even at room temperature and after 1 month at a storage temperature of 45° C. and had decomposed after 3 freeze-thaw cycles at −15° C.

Preparation of the emulsions

The water phase heated to from 80 to 85° C. was introduced into the oil phase in the same temperature with vigorous stirring and cooled to 25 to 30° C. with vigorous stirring. If the mean size of the dispersed water droplets exceeds 1 to 2 μm, homogenization must be carried out using an emulsification machine which operates on the rotor-stator principle.

I) Emulsions of flowable consistency (lotions)
Oil phases (composition)

|  | Fm 1 | Fm 2 | Fm 3 | Fm 4 | Fm 5 | Comp. Fm 6 |
|---|---|---|---|---|---|---|
| Emulsifier | 3.0% | 3.0% | 3.0% | 3.0% | 3.0% | 3.0% |
| Castor oil, hydrogenated | 0.3% | 0.3% | 0.3% | 0.3% | 0.3% | 0.3% |
| Microwax (Lunacea M) | 0.2% | 0.2% | 0.2% | 0.2% | 0.2% | 0.2% |
| Paraffin oil (30 mPas) | 10.5% | 10.0% | — | — | — | — |
| Isohexadecane | 10.0% | — | — | — | — | — |
| Isohexadecyl palmitate | — | — | 10.5% | — | — | — |
| Isooctyl palmitate | — | 13.5% | — | — | — | — |
| Cetyl isooctanoate | — | — | 11.0% | — | — | — |
| Decyl oleate | — | — | — | 10.5% | — | — |
| Isopropyl palmitate | — | — | — | 11.0% | — | — |
| C$_{8/10}$-triglyceride | — | — | — | — | 23.5% | 23.5% |
| Oil phase | 24.0% | 27.0% | 25.0% | 25.0% | 27.0% | 27.0% |

Water phases (composition)
0.3% of magnesium sulfate, 2.0% of glycerol, Water to 100% Fm 4 additionally contained 2% of the moisturizer Lactil® (Th. Goldschmidt AG, aqueous solution of sodium pyrrolidonecarboxylate, sodium lactate, urea and amino acids).

II) Emulsions of pasty consistency (creams)

|  | Fm 1 | Fm 2 | Fm 3 | Fm 4 | Fm 5 | Fm 6 | Fm 7 | Comp. Fm 8 |
|---|---|---|---|---|---|---|---|---|
| Oil Phase | | | | | | | | |
| Emulsifier | 3.0% | 3.0% | 3.0% | 3.0% | 3.0% | 3.0% | 3.0% | 3.0% |
| Castor Oil hydrogenated | 0.8% | 0.8% | 0.5% | 0.5% | 0.8% | 0.8% | 0.8% | 0.5% |
| Beeswax | 1.2% | 1.2% | 0.5% | 0.5% | 1.2% | 1.2% | 1.2% | 0.5% |
| Neo-Heliopan AV | 4.0% | — | — | — | — | — | — | — |
| Parsol 1789 | 2.0% | — | — | — | — | — | — | — |
| Alkyl benzoate | 9.5% | — | — | — | — | — | — | — |
| C$_{8/10}$-triglyceride | 9.5% | — | 16.0% | — | — | — | — | 16.0% |
| Avocado Oil | — | — | 10.0% | — | — | — | — | 10.0% |
| Paraffin Oil (30 mPas) | — | — | — | 9.0% | 10.0% | — | — | — |
| Cetyl octanoate | — | 10.0% | — | — | — | — | 11.0% | — |
| Hexadecyl palmitate | — | 10.0% | — | — | — | — | — | — |
| Octyl palmitate | — | — | — | 10.0% | — | 20.0% | — | — |
| Isohexadecane | — | — | — | — | 10.0% | — | — | — |
| Octyl octanoate | — | — | — | — | — | — | 7.0% | — |
|  | 30.0% | 25.0% | 30.0% | 23.0% | 25.0% | 25.0% | 23.0% | 30.0% |
| Water Phase | | | | | | | | |
| Magnesium sulfate | 0.3% | 0.3% | 0.3% | 0.3% | 0.3% | 0.3% | 0.3% | 0.3% |
| Glycerol | 2.0% | 2.0% | 2.0% | 2.0% | 3.0% | 3.0% | 3.0% | 2.0% |
| Urea | — | 2.0% | — | — | — | — | — | — |

-continued

| II) Emulsions of pasty consistency (creams) | | | | | | | |
| --- | --- | --- | --- | --- | --- | --- | --- |
| | Fm 1 | Fm 2 | Fm 3 | Fm 4 | Fm 5 | Fm 6 | Fm 7 | Comp. Fm 8 |

| | Fm 1 | Fm 2 | Fm 3 | Fm 4 | Fm 5 | Fm 6 | Fm 7 | Comp. Fm 8 |
| --- | --- | --- | --- | --- | --- | --- | --- | --- |
| Oil Phase Ethanol (96%) | — | — | — | — | 10.0% | 10.0% | 10.0% | — |
| Water | 67.7% 70.0% | 70.0% 75.0% | 67.7% 70.0% | 74.7% 77.0% | 61.7% 75.0% | 61.7% 75.0% | 63.7% 77.0% | 67.7% 70.0% |

2.2 Use as dispersion auxiliary

The polyglycerol partial esters according to the invention having an HLB value of from 3 to 7 are suitable as dispersion auxiliaries for inorganic pigments in bodies of oil.

Suitable inorganic pigments are all customary main-group metal and transition metal oxides, such as, for example, iron oxide, titanium dioxide, zinc oxide and cerium oxide, in each case also in their micronized form.

EXAMPLE 72 g of octyl palmitate was introduced into a high speed mill with spherical grinding media, and 28 g of microfine titanium dioxide, 6 g of polyglycerol partial ester and 4 g of Aerosil R972 (Degussa) was added with stirring. After grinding for 30 minutes, a finely divided, while dispersion was obtained, from which the $TiO_2$ did not settle out even after a storage time of 6 weeks.

COMPARATIVE EXAMPLE 72 g of octyl palmitate was introduced into a high-speed mill with spherical grinding media, and 28 g of microfine titanium dioxide and 4 g of Aerosil R972 was added with stirring. After grinding for 30 minutes, a dispersion was obtained which had an inhomogeneous appearance and from which a finely divided sediment of $TiO_2$ pigment settled out after standing for several hours.

What is claimed is:

1. A polyglycerol partial ester comprising the estenification product of a polyglycerol mixture; saturated or unsaturated, linear or branch fatty acids having 12–22 carbon atoms; and dimer acids obtained by dimerization of fatty acids from vegetable oils having a mean functionality of from 2 to 2.4, wherein the overall degree of esterification of the polyglycerol mixture is between 30% and 75%, and wherein the degree of esterification of the polyglycerol mixture with the dimer acids is between 5% and 50%.

2. A polyglycerol partial ester as claimed in claim 1, wherein the polyglycerol has a mean degree of condensation of at least 2.

3. A polyglycerol partial ester as claimed in claim 1, wherein the polyglycerol has a mean degree of condensation of from 3 to 4.

4. A cosmetic or pharmaceutical preparation comprising a water-in-oil emulsifier, said emulsifier being said polyglycerol partial ester of claim 1.

5. A cosmetic or pharmaceutical preparation comprising a water-in-oil emulsifier, said emulsifier being said polyglycerol partial ester of claim 2.

6. A cosmetic or pharmaceutical preparation comprising a water-in-oil emulsifier, said emulsifier being said polyglycerol partial ester of claim 3.

7. A dispersion comprising an inorganic micropigment; an oil and, as a dispersant of said inorganic micropigment in said oil, said polyglycerol partial ester of claim 1.

8. A dispersion comprising an inorganic micropigment, an oil and, as a dispersant of said inorganic micropigment in said oil, said polyglycerol partial ester of claim 2.

9. A dispersion comprising an inorganic micropigment, an oil and, as a dispersant of said inorganic micropigment in said oil, said polyglycerol partial ester of claim 3.

10. A process for preparing a polyglycerol partial ester comprising the steps of:
   (a) reacting technical grade polyglycerol with saturated or unsaturated, linear or branched fatty acids having 12 to 22 carbon atoms such that the degree of esterification of the polyglycerol is in the range of between 25% and 60%; and
   (b) reacting the product of step (a) with dimer acids obtained by dimerization of fatty acids from vegetable oils such that the overall degree of esterification is in the range of between 30% and 75%.

* * * * *